United States Patent
Chen et al.

(10) Patent No.: US 11,547,311 B2
(45) Date of Patent: Jan. 10, 2023

(54) PHYSIOLOGICAL DATA DETECTION METHOD AND WEARABLE DEVICE THEREFOR

(71) Applicant: ASUSTEK COMPUTER INC., Taipei (TW)

(72) Inventors: Yu-Jen Chen, Taipei (TW); Chun-Hsiang Tsai, Taipei (TW)

(73) Assignee: ASUSTEK COMPUTER INC., Taipei (TW)

( * ) Notice: Subject to any disclaimer, the term of this patent is extended or adjusted under 35 U.S.C. 154(b) by 362 days.

(21) Appl. No.: 16/864,463

(22) Filed: May 1, 2020

(65) Prior Publication Data
US 2020/0345253 A1 Nov. 5, 2020

(30) Foreign Application Priority Data
May 3, 2019 (TW) ................................ 108115432

(51) Int. Cl.
*A61B 5/00* (2006.01)
*A61B 5/024* (2006.01)
*A61B 5/352* (2021.01)

(52) U.S. Cl.
CPC .......... *A61B 5/02427* (2013.01); *A61B 5/352* (2021.01); *A61B 5/681* (2013.01); *A61B 5/6824* (2013.01); *A61B 5/6826* (2013.01)

(58) Field of Classification Search
CPC . A61B 5/02427; A61B 5/024; A61B 5/02405; A61B 5/02416; A61B 5/352; A61B 5/681; A61B 5/6824; A61B 5/6826; A61B 5/7221
See application file for complete search history.

(56) References Cited

U.S. PATENT DOCUMENTS

| | | | |
|---|---|---|---|
| 3,759,248 A * | 9/1973 | Valiquette | A61B 5/364 600/516 |
| 2017/0071482 A1* | 3/2017 | Chang | A61B 5/02416 |
| 2018/0242876 A1 | 8/2018 | Hughes et al. | |
| 2020/0000349 A1* | 1/2020 | Lin | A61B 5/30 |

FOREIGN PATENT DOCUMENTS

| | | |
|---|---|---|
| CN | 102946943 A | 2/2013 |
| TW | I439255 B | 6/2014 |
| TW | M561501 U | 6/2018 |
| TW | I653029 B | 3/2019 |
| WO | WO-2015/171667 A1 | 11/2015 |
| WO | WO-2017/024457 A1 | 2/2017 |

* cited by examiner

*Primary Examiner* — Scott M. Getzow
(74) *Attorney, Agent, or Firm* — Muncy, Geissler, Olds & Lowe, P.C.

(57) ABSTRACT

A physiological data detection method is provided. The physiological data detection method includes the following steps. Firstly, an ECG signal and a PPG signal are detected. Then, a plurality of RRI values is calculated according to the ECG signal, and a plurality of PPI values is calculated according to the PPG signal. Thereafter, wrong RRI values are excluded according to the RRI values and/or the PPI values. Then, whether an abnormal state occurs or not is determined by using the remaining RRI values. A wearable device therefor is also provided.

11 Claims, 6 Drawing Sheets

PHYSIOLOGICAL DATA DETECTION METHOD AND WEARABLE DEVICE THEREFOR

CROSS-REFERENCE TO RELATED APPLICATION

This application claims the priority benefit of Taiwan Application Serial No. 108115432, filed on May 3, 2019. The entirety of the above-mentioned patent application is hereby incorporated by reference herein and made a part of specification.

BACKGROUND OF THE INVENTION

Field of the Invention

The disclosure relates to a wearable device.

Description of the Related Art

In a conventional arrhythmia detection method, physiological data is used to determine whether arrhythmia occurs or not, and the physiological data is obtained mainly by using an electrocardiogram. However, the judgment based on electrocardiogram data may be incorrect, and a medical institution usually alternatively arrange a 24-hour electrocardiogram examination machine for the patient to carry, in order to observe whether there are obvious heart rhythm changes or not and determine whether arrhythmia occurs or not as well as the severity of arrhythmia. Therefore, the conventional arrhythmia detection method is time-consuming and causes inconvenience to the patient's daily life.

BRIEF SUMMARY OF THE INVENTION

The disclosure provides a physiological data detection method. The physiological data detection method includes the following steps. Firstly, an electrocardiography (ECG) signal and a photoplethysmography (PPG) signal are detected. Then, a plurality of R-R interval (RRI) values is calculated according to the ECG signal, and a plurality of peak-peak interval (PPI) values is calculated according to the PPG signal. Thereafter, wrong RRI values are excluded according to the RRI values and/or the PPI values. Then, it is determined whether a difference value between two adjacent RRI values in the remaining RRI values is greater than a preset value or not, and when the difference value is greater than the preset value, it is determined that an abnormal state occurs.

The disclosure further provides a wearable device for physiological data detection. The wearable device for physiological data detection includes an ECG detection module, a PPG detection module, and a calculation unit. The ECG detection module is configured to detect an ECG signal. The PPG detection module is configured to detect a PPG signal. The calculation unit is electrically connected to the ECG detection module and the PPG detection module. The calculation unit calculates a plurality of RRI values according to the ECG signal, and calculates a plurality of PPI values according to the PPG signal. The calculation unit excludes wrong RRI values according to the RRI values and/or the PPI values and determines whether a difference value between two adjacent RRI values in the remaining RRI values is greater than a preset value or not. When the difference value is greater than the preset value, the calculation unit determines that an abnormal state occurs.

Specific embodiments of the disclosure will be further described by using the following examples and drawings.

DETAILED DESCRIPTION OF THE EMBODIMENTS

Specific embodiments of the disclosure will be described in further detail below with reference to schematic drawings. The advantages and features of the disclosure will become more apparent from the following description and claims. It should be noted that the drawings are all in a very simplified form and are not drawn to accurate scale, but are merely used for convenience and clarity of description of the embodiments of the disclosure.

Figure 1:
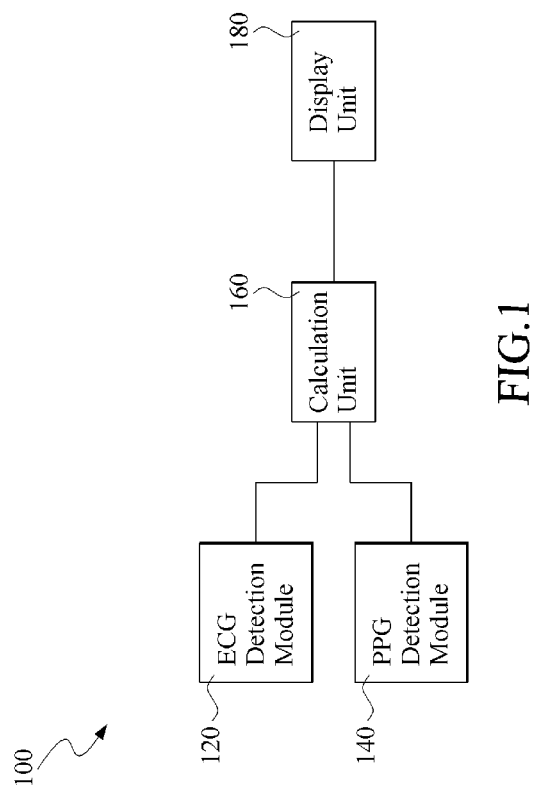
FIG. 1 is a schematic block diagram of a wearable device for physiological data detection according to the disclosure.
Figure 2A:
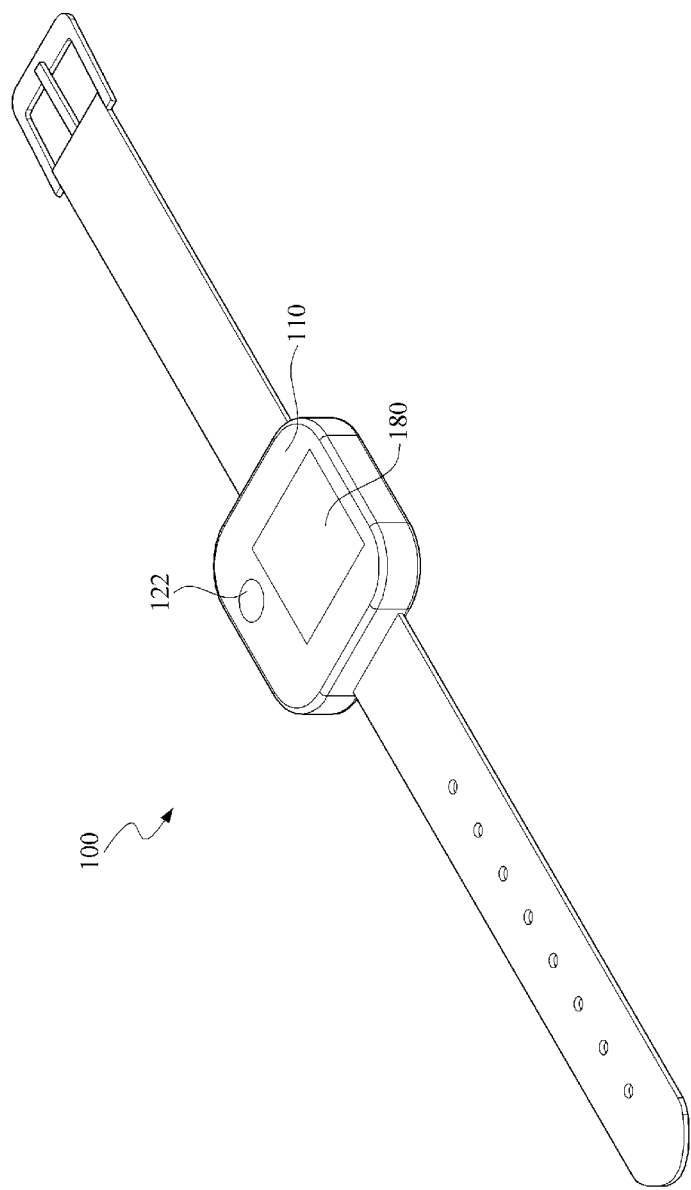
FIG. 2A and FIG. 2B are three-dimensional diagrams of physiological data detection by the wearable device for shown in FIG. 1.
Figure 2B:
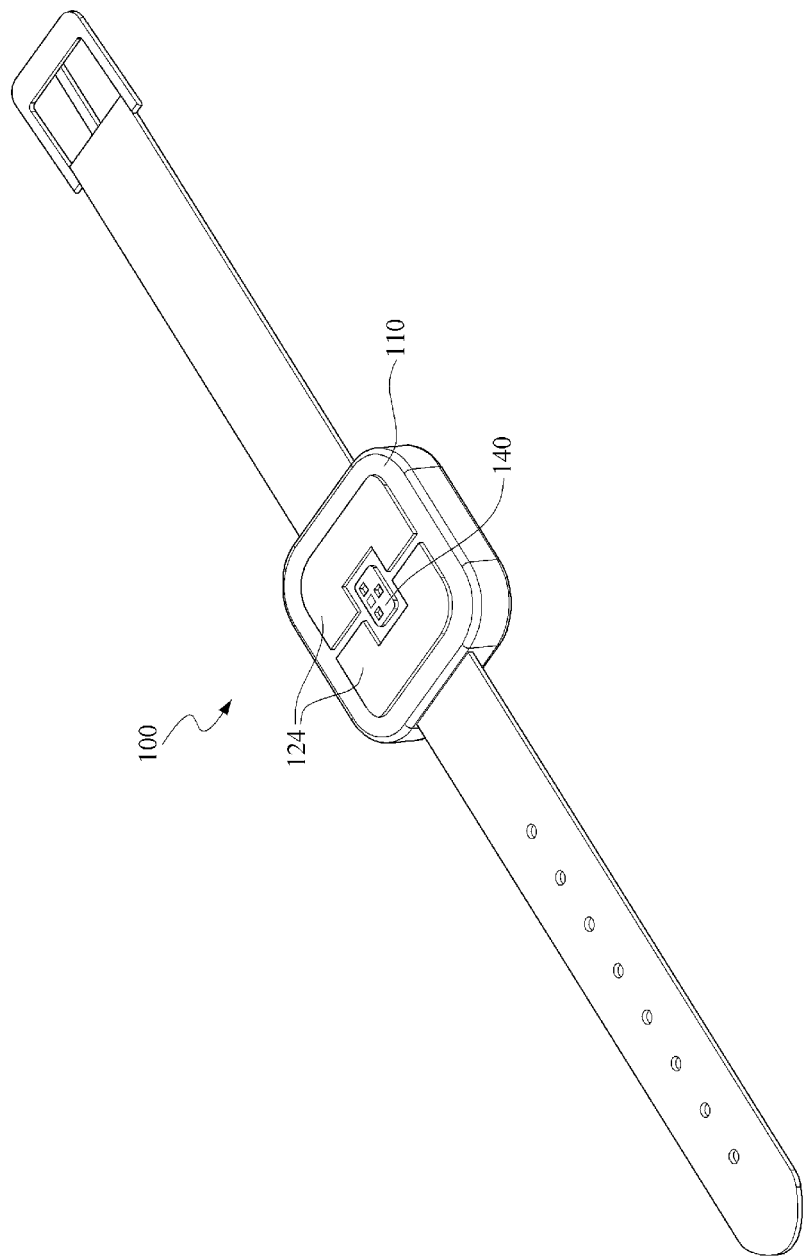
Figure 3:
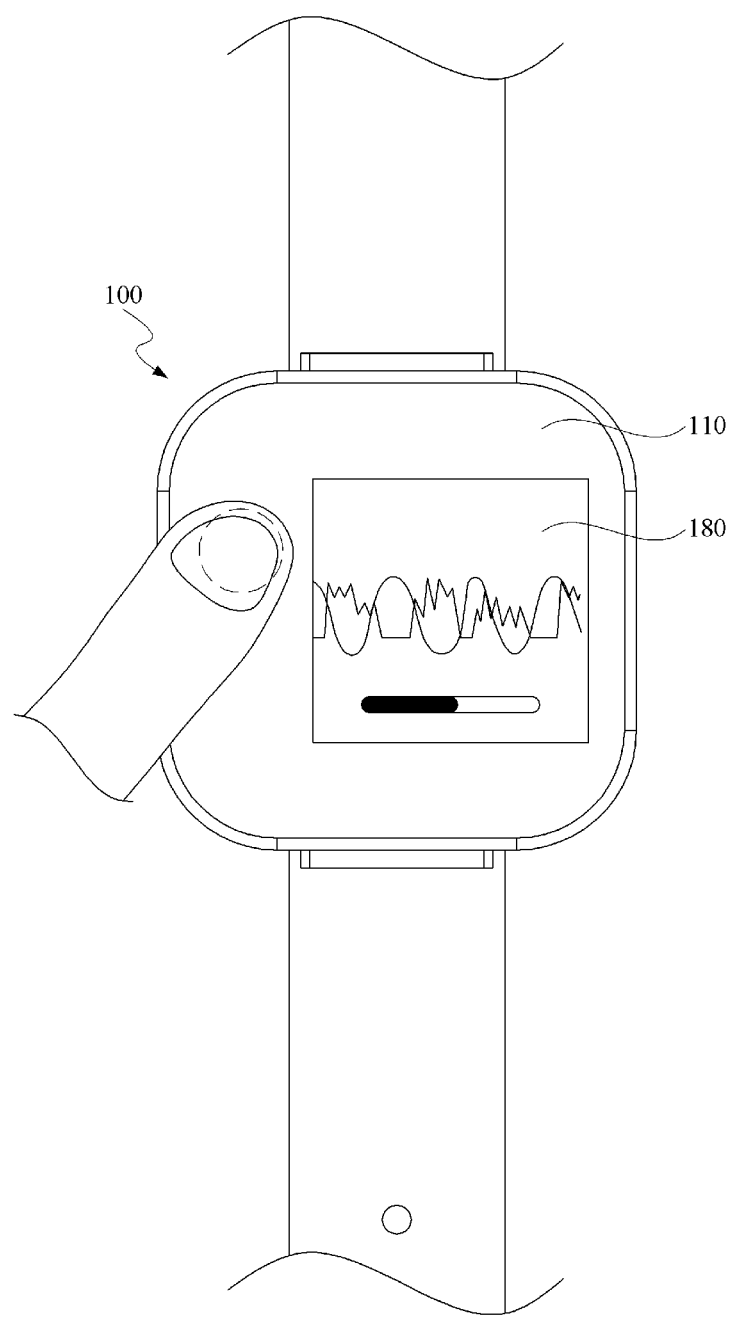
FIG. 3 is a schematic diagram of an embodiment in which a user operates physiological data detection by the wearable device shown in FIG. 1.

FIG. 1 is a schematic block diagram of an embodiment of a wearable device for physiological data detection according to the disclosure. FIG. 2A and FIG. 2B are three-dimensional diagrams of an embodiment of the wearable device for physiological data detection shown in FIG. 1. FIG. 3 is a schematic diagram of an embodiment in which a user or a subject operates physiological data detection by the wearable device that shown in FIG. 1. The wearable device for physiological data detection may be an electronic watch, a smart band, a skin patch or other electronic device which is wearable or adapted for contact with a human body to detect a pulse. Descriptions are made by using a wrist-type heart rhythm detection device as an example in the drawings.

As shown in FIG. 1, the wearable device for physiological data detection 100 includes an electrocardiography (ECG) detection module 120, a photoplethysmography (PPG) detection module 140, a calculation unit 160, and a display unit 180.

The ECG detection module 120 is configured to detect an ECG signal, and the PPG detection module 140 is configured to detect a PPG signal. The calculation unit 160 is electrically connected to the ECG detection module 120 and the PPG detection module 140 to receive the ECG signal and the PPG signal, to determine whether arrhythmia occurs or not. The display unit 180 is electrically connected to the calculation unit 160 to present a determining result of the calculation unit 160.

In an embodiment, the calculation unit 160 is a processing unit, and the display unit 180 is a liquid crystal display module, an organic light-emitting diode display module, or an electronic ink display module. Details about the determining of whether arrhythmia occurs or not by the calculation unit 160 according to the ECG signal and the PPG signal will be further described in the following paragraphs corresponding to FIG. 4.

Refer to FIG. 2A and FIG. 2B. FIG. 2A and FIG. 2B are three-dimensional diagrams of an embodiment of the wearable device for physiological data detection shown in FIG. 1. FIG. 2A is a three-dimensional front view of the wearable device for physiological data detection 100, and FIG. 2B is a three-dimensional rear view of the wearable device for physiological data detection 100. As shown in the figures, in an embodiment, the ECG detection module 120 includes two ECG electrodes 122 and 124, to constitute a single-lead ECG sensor. The two ECG electrodes 122 and 124 are respectively disposed on a front side (that is, the surface away from the wrist) and a back side (that is, the surface facing toward the wrist) of a housing 110 of the wearable device for physiological data detection. The PPG detection module 140 is disposed on the back side of the housing 110 of the wearable device for physiological data detection to detect the PPG signal at a wrist of the subject.

As shown in FIG. 3, when the subject presses the ECG electrode 122 located on the front side of the housing 110 of the wearable device for physiological data detection with a finger, the ECG electrode 124 located on the back side of the housing 110 of the wearable device for physiological data detection is in contact with the wrist of the other hand of the subject. In this way, an ECG signal of the subject is generated. At the same time, the PPG detection module 140 located on the back side of the housing 110 of the wearable device for physiological data detection detects a PPG signal at the wrist of the subject.

As shown in FIG. 2A and FIG. 2B, the wearable device for physiological data detection in this embodiment only includes a PPG detection module 140, disposed on the back side of the housing 110 of the wearable device for physiological data detection to detect the PPG signal at the wrist of the subject. In an embodiment, in addition to the PPG detection module 140 disposed on the back side of the housing 110 of the wearable device for physiological data detection in the figures, another PPG detection module is further disposed on the front side or a side surface of the housing 110, to detect a finger PPG signal of the subject. In this way, a finger PPG signal and a wrist PPG signal of the subject are obtained at the same time, thereby enhancing the accuracy of the PPG signals.

The wearable device for physiological data detection 100 in the foregoing embodiment presents, to the subject, the determining result of the calculation unit 160 through the display unit 180. In an embodiment, the wearable device for physiological data detection presents, the subject, the determining result of the calculation unit 160 in an audio manner, or transmits the determining result of the calculation unit 160 to another electronic device such as a mobile phone or a notebook computer, for subsequent statistics collection and processing.

Figure 4:
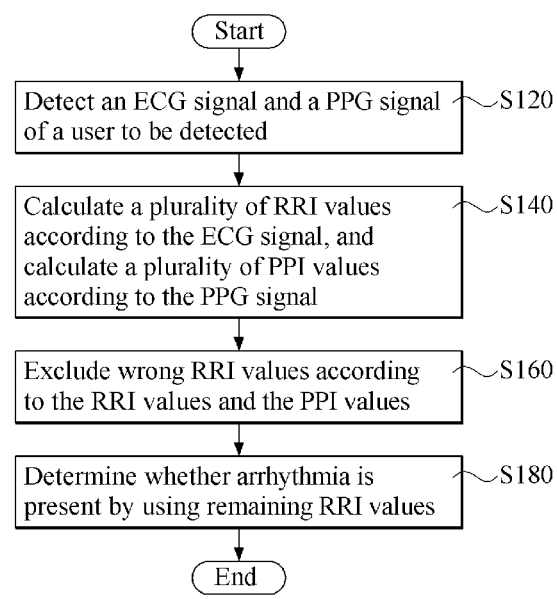
FIG. 4 is a flowchart of an embodiment of a physiological data detection method according to the disclosure.

FIG. 4 is a flowchart of an embodiment of a physiological data detection method according to the disclosure. The physiological data detection method is applicable to the wearable device for physiological data detection 100 shown in FIG. 1. Any device configured to provide an ECG signal and a PPG signal of the subject at the same time is applicable to the physiological data detection method in this embodiment, to detect a heart rhythm of the subject and further determine whether an abnormal heart rhythm or arrhythmia occurs or not. The physiological data detection method will be described below by using an example in which the subject performs physiological data detection by using the wearable device for physiological data detection 100 shown in FIG. 1. As shown in the figure, the physiological data detection method includes the following steps.

Firstly, as described in step S120, an ECG signal of the subject is detected by using the ECG detection module 120, and a PPG signal of the subject is detected by using the PPG detection module 140.

Figure 5:
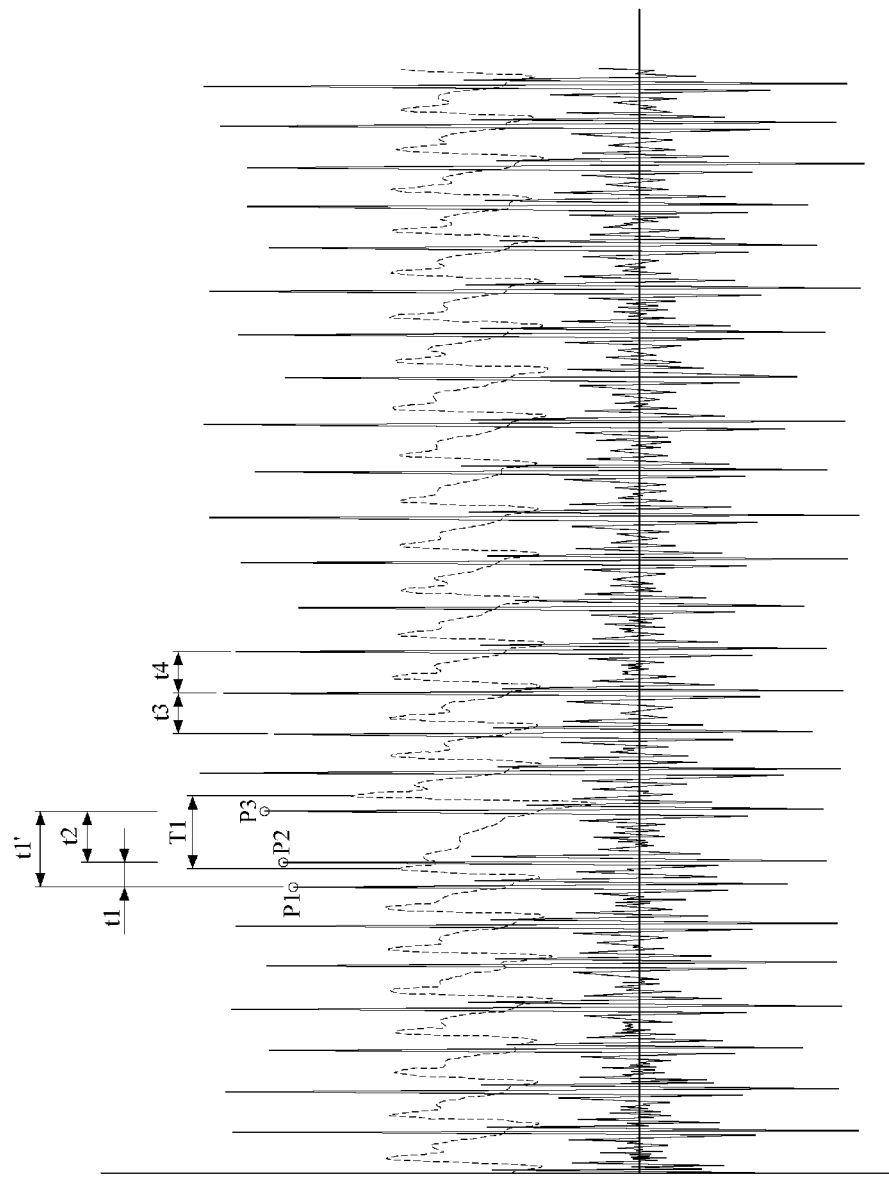
FIG. 5 is a waveform graph showing an embodiment of an ECG signal and a PPG signal obtained in step S120 in FIG. 4.

Refer to FIG. 5. FIG. 5 is a waveform graph showing an embodiment of an ECG signals and a PPG signal obtained in step S120 in FIG. 4, where the ECG signal is indicated by a solid line, and the PPG signal is indicated by a dashed line. Because the ECG signal and the PPG signal of the subject are detected at the same time in step S120, peaks of the ECG signal and peaks of the PPG signal shown in the figure have a correspondence. In addition, because time is needed for pumping blood from the heart to the arm, the peaks of the PPG signal generally appear slightly later than the peaks of the ECG signal.

In an embodiment, the ECG signal detected in step S120 is a single-lead ECG signal, that is, an ECG signal detected by using the two ECG electrodes, to simplify the detection complexity.

In an embodiment, the PPG signal detected in step S120 is a wrist PPG signal. The wrist PPG signal is a right-wrist PPG signal or a left-wrist PPG signal. In an embodiment, the PPG signal is a finger PPG signal.

Secondly, a single PPG signal is detected in step S120. In an embodiment, PPG signals at a plurality of different body positions of the subject are detected in step S120, to improve the accuracy of the obtained PPG signals. In an embodiment, a wrist PPG signal and a finger PPG signal of the subject are detected in the step at the same time, thereby improving the accuracy of examination.

Then, as described in step S140, by using the calculation unit 160, a plurality of R-R interval (RRI) values is calculated according to the ECG signal, and a plurality of peak-peak interval (PPI) values is calculated according to the PPG signal. As shown in FIG. 5, the RRI values are time interval values between the peaks of the ECG signal detected in step S120, which are t1, t2, t3, and t4 in the figure. The PPI values are time interval values between the peaks of the PPG signal detected in step S120, which are T1 in the figure.

Then, as described in step S160, wrong RRI values in the RRI values are excluded by using the calculation unit 160 according to the RRI values and/or the PPI values calculated in step S140.

In an embodiment, referring to FIG. 5, the RRI values are compared with the corresponding PPI values in step S160, to exclude wrong RRI values. In an embodiment, t1 is compared with T1. Generally, when more accurate detection data is provided than the PPG signal, the RRI value that calculated according to the ECG signal is likely to have an error due to the data variation of the state of the subject. Noise or a peak generated when the subject is scared is likely to be incorrectly determined as a peak of an electrocardiogram R wave. Therefore, the comparison of the RRI values with the corresponding PPI values helps exclude wrong RRI values in the RRI values, to obtain more accurate values and avoid misjudgment. In an embodiment, as shown in the figure, there is an obvious difference between the RRI value t1 and the corresponding PPI value T1, and therefore, the RRI value t1 is probably a wrong value and needs to be excluded.

In an embodiment, each RRI value is compared with an average value of the RRI values to exclude the wrong RRI values in step S160. The average value is an average value of all RRI values obtained within a detection time (which is 1 minute in an embodiment) in step S120. Generally, an RRI value of the subject, either normal or abnormal, falls within a range. An RRI value not falling within the range is probably a wrong RRI value. Therefore, the comparison of each RRI value with the average value of the RRI values helps exclude the wrong RRI values, to obtain more accurate values and avoid misjudgment. In an embodiment, as shown in FIG. 5, the RRI value t1 is obviously less than the average value of all the PPI values within the detection time (which is an average value of all the PPI values shown in the figure in an embodiment), and therefore, the RRI value t1 is probably a wrong value and needs to be excluded.

In an embodiment, for the identified wrong RRI value, that is, t1 shown in the figure, in step S160, a wrong peak P2 is determined from the RRI value t1, and the peak P2 is excluded, to generate a modified RRI value t1' to replace the wrong RRI value t1, that is, a correct RRI value t1' is calculated by using a peak P1 and a peak P3 on two sides of P2 in the figure, to replace the RRI value t1. In an embodiment, to accelerate a processing program, the wrong RRI value t1 is directly excluded in step S160, and another corrected value is not supplemented.

Then, as described in step S180, it is determined, according to the remaining RRI values left after wrong RRI values are excluded, whether an abnormal state such as arrhythmia occurs or not. In an embodiment, referring to FIG. 5, in step S180, it is determined whether a difference value between two adjacent RRI values (t3 and t4) in the remaining RRI values satisfies a preset condition or not after the wrong RRI values (t1) are excluded. When the difference value satisfies the preset condition, it is determined that an abnormal state occurs; when the difference value does not satisfy the preset condition, the heart rhythm state is normal. In an embodiment, when the difference value between the two adjacent RRI values in the RRI values reaches 30% (that is, the preset condition), it is determined that the heart rhythm of the subject is abnormal; otherwise, it is determined that the heart rhythm of the subject is normal. In addition, to further avoid misjudgment, in an embodiment, in step S180, the heart rhythm of the subject is determined to be abnormal, only when the difference value between the two adjacent RRI values reaches 30% for a plurality of times.

In an embodiment, as shown in FIG. 5, when whether an abnormal state occurs or not is determined only according to the ECG signal without excluding the wrong RRI value t1, the heart rhythm of the subject is likely to be determined to be abnormal due to the existence of the RRI values t1 and t2. Once the wrong RRI values are excluded, misjudgment is avoided.

In the physiological data detection method, after the determining step is completed, a determining result is presented on the display unit 180 of the wearable device. In an embodiment, in the physiological data detection method, the determining result is presented in an audio manner, or the determining result is transmitted to another electronic device such as a mobile phone or a notebook computer, for subsequent statistics collection and processing.

Compared with the conventional arrhythmia detection method, the physiological data detection method and the wearable device therefor according to the disclosure provides the subject to make a judgment by using the lightweight wearable device and reduce the detection time to avoid inconvenience caused to the user's daily life.

The foregoing descriptions are merely preferred embodiments of the disclosure and are not intended to limit the disclosure in any way. Any person skilled in the art can make any form of equivalent replacement or modification to the technical means and technical contents disclosed by the disclosure without departing from the scope of the technical means of the disclosure, and such equivalent replacement or modification does not depart from the contents of the technical means of the present disclosure and still falls within the protection scope of the disclosure.

What is claimed is:

1. A physiological data detection method, comprising:
   detecting an electrocardiography (ECG) signal;
   detecting a photoplethysmography (PPG) signal;
   calculating a plurality of R-R interval (RRI) values according to the ECG signal;
   calculating a plurality of peak-peak interval (PPI) values according to the PPG signal;
   excluding wrong RRI values according to the RRI values and/or the PPI values; and
   determining whether a difference value between two adjacent RRI values in the remaining RRI values is greater than a preset value or not, and when the difference value is greater than the preset value, determining that an abnormal state occurs;
   wherein the step of excluding wrong RRI values according to the RRI values and/or the PPI values comprises: comparing the RRI values with the corresponding PPI values.

2. The physiological data detection method according to claim 1, wherein the ECG signal is a single-lead ECG signal.

3. The physiological data detection method according to claim 1, wherein the PPG signal is a wrist PPG signal or a finger PPG signal.

4. The physiological data detection method according to claim 1, wherein the step of excluding wrong RRI values according to the RRI values and/or the PPI values comprises: comparing each RRI value with an average value of the RRI values.

5. A wearable device for physiological data detection, comprising:
   an ECG detection module, configured to detect an ECG signal;
   a PPG detection module, configured to detect a PPG signal; and
   a calculation unit, electrically connected to the ECG detection module and the PPG detection module, and configured to:
   calculate a plurality of RRI values according to the ECG signal, and calculate a plurality of PPI values according to the PPG signal;
   exclude wrong RRI values according to the RRI values and/or the PPI values; and
   determine whether a difference value between two adjacent RRI values in the remaining RRI values is greater than a preset value or not, and when the difference value is greater than the preset value, determine that an abnormal state occurs;
   wherein the calculation unit compares the RRI values with the corresponding PPI values, to exclude the wrong RRI values.

6. The wearable device for physiological data detection according to claim 5, further comprising a display unit, electrically connected to the calculation unit to present a determining result of the calculation unit.

7. The wearable device for physiological data detection according to claim 5, wherein the ECG signal is a single-lead ECG signal.

8. The wearable device for physiological data detection according to claim 5, wherein the PPG signal is a wrist PPG signal or a finger PPG signal.

9. The wearable device for physiological data detection according to claim 5, wherein the calculation unit compares each RRI value with an average value of the RRI values, to exclude the wrong RRI values.

10. The wearable device for physiological data detection according to claim 5, further comprising a housing, wherein the ECG detection module comprises two ECG electrodes, respectively disposed on a front side and a back side of the housing.

11. The wearable device for physiological data detection according to claim 10, wherein the PPG detection module is disposed on the front side or the back side of the housing.

* * * * *